(12) United States Patent
Vanderpool et al.

(10) Patent No.: US 11,857,218 B2
(45) Date of Patent: *Jan. 2, 2024

(54) SUBCUTANEOUS DELIVERY TOOL

(71) Applicant: Medtronic, Inc., Minneapolis, MN (US)

(72) Inventors: Matthew T. Vanderpool, Minneapolis, MN (US); Michael R. Klardie, Bloomington, MN (US); Kris A. Peterson, St. Louis Park, MN (US)

(73) Assignee: Medtronic, Inc., Minneapolis, MN (US)

( * ) Notice: Subject to any disclaimer, the term of this patent is extended or adjusted under 35 U.S.C. 154(b) by 541 days.

This patent is subject to a terminal disclaimer.

(21) Appl. No.: 17/000,688

(22) Filed: Aug. 24, 2020

(65) Prior Publication Data
US 2020/0383702 A1    Dec. 10, 2020

Related U.S. Application Data

(63) Continuation of application No. 15/610,076, filed on May 31, 2017, now Pat. No. 10,786,279, which is a
(Continued)

(51) Int. Cl.
*A61B 17/34* (2006.01)
*A61B 17/3209* (2006.01)
(Continued)

(52) U.S. Cl.
CPC ............ *A61B 17/3468* (2013.01); *A61B 5/29* (2021.01); *A61B 17/32093* (2013.01);
(Continued)

(58) Field of Classification Search
CPC .......... A61B 17/3468; A61B 17/32093; A61B 2017/320044; A61B 2017/320056; A61B 5/283; A61N 1/37205; A61N 1/3756
See application file for complete search history.

(56) References Cited

U.S. PATENT DOCUMENTS 2,009,393 A    7/1935   Gioacchino
2,647,512 A *  8/1953   Johnson ................ A61M 31/00
                                                            604/64
(Continued)

FOREIGN PATENT DOCUMENTS

CN    1031481 A    3/1989
CN    2621634 Y    6/2004
(Continued)

OTHER PUBLICATIONS

Prosecution History from U.S. Appl. No. 14/204,227, dated Nov. 5, 2015 through Sep. 8, 2021, 486 pp.
(Continued)

*Primary Examiner* — Jing Rui Ou
(74) *Attorney, Agent, or Firm* — Shumaker & Sieffert, P.A.

(57) ABSTRACT

Subcutaneous implantation tools and methods of implanting a subcutaneous device using the same. The tool may include a tool body having a longitudinally extending recess having a distal opening and having a tunneler at a distal end of the tool body extending from the distal opening of the recess. The tool may include a plunger slidably fitting within at least a portion of the tool body recess. The recess may be configured to receive an implantable device and the tunneler preferably extends distally from the recess at a position laterally displaced from the device when the device is so located in the recess. Movement of the plunger distally within the recess advances the device distally out of the recess and alongside of and exterior to the tunneler.

20 Claims, 9 Drawing Sheets

Related U.S. Application Data continuation of application No. 14/204,227, filed on Mar. 11, 2014, now Pat. No. 11,311,312.

(60) Provisional application No. 61/788,940, filed on Mar. 15, 2013.

(51) Int. Cl.
    *A61B 5/29*     (2021.01)
    *A61N 1/375*     (2006.01)
    *A61B 17/32*     (2006.01)
    *A61N 1/372*     (2006.01)

(52) U.S. Cl.
    CPC .............. *A61B 2017/320044* (2013.01); *A61B 2017/320056* (2013.01); *A61N 1/3756* (2013.01); *A61N 1/37205* (2013.01)

(56) References Cited

U.S. PATENT DOCUMENTS

| | | | |
|---|---|---|---|
| 4,915,686 | A | 4/1990 | Frederick |
| 5,127,404 | A | 7/1992 | Wyborny et al. |
| 5,304,119 | A | 4/1994 | Balaban et al. |
| 5,484,403 | A | 1/1996 | Yoakum et al. |
| 5,507,807 | A * | 4/1996 | Shippert .............. A61M 31/00 604/59 |
| 5,562,613 | A | 10/1996 | Kaldany |
| 5,772,671 | A | 6/1998 | Harmon |
| 5,842,999 | A | 12/1998 | Pruitt et al. |
| 5,954,670 | A | 9/1999 | Baker |
| 5,987,352 | A | 11/1999 | Klein et al. |
| 6,230,059 | B1 | 5/2001 | Duffin |
| 6,412,490 | B1 | 7/2002 | Lee |
| 7,035,684 | B2 | 4/2006 | Lee |
| 8,888,745 | B2 | 11/2014 | Van Der Graaf et al. |
| 10,786,279 | B2 * | 9/2020 | Vanderpool ........ A61B 17/3468 |
| 11,134,986 | B2 * | 10/2021 | Vanderpool ........ A61B 17/3468 |
| 11,241,253 | B2 * | 2/2022 | Vanderpool ...... A61B 17/32093 |
| 2001/0029386 | A1 | 10/2001 | Matsutani et al. |
| 2003/0088212 | A1 | 5/2003 | Tal |
| 2004/0082969 | A1 | 4/2004 | Kerr |
| 2004/0143284 | A1 | 7/2004 | Chin |
| 2004/0193154 | A1 | 9/2004 | Leatherbury et al. |
| 2004/0249388 | A1 | 12/2004 | Michelson |
| 2005/0090852 | A1 | 4/2005 | Layne et al. |
| 2005/0096645 | A1 | 5/2005 | Wellman et al. |
| 2005/0107768 | A1 | 5/2005 | Ting |
| 2006/0074434 | A1 | 4/2006 | Wenstrom, Jr. et al. |
| 2006/0097331 | A1 | 5/2006 | Hattori et al. |
| 2006/0106415 | A1 | 5/2006 | Gabbay |
| 2006/0174898 | A1 | 8/2006 | Brown |
| 2007/0010738 | A1 | 1/2007 | Mark et al. |
| 2007/0179515 | A1 | 8/2007 | Matsutani et al. |
| 2007/0249992 | A1 | 10/2007 | Bardy |
| 2008/0154298 | A1 | 6/2008 | Grayzel et al. |
| 2009/0030426 | A1 | 1/2009 | Zinn et al. |
| 2009/0036917 | A1 | 2/2009 | Anderson |
| 2009/0137946 | A1 | 5/2009 | Nassiri et al. |
| 2010/0030227 | A1 | 2/2010 | Kast et al. |
| 2010/0094252 | A1 | 4/2010 | Wengreen et al. |
| 2010/0198140 | A1 | 8/2010 | Lawson |
| 2010/0324578 | A1 | 12/2010 | Bardy |
| 2010/0331868 | A1 | 12/2010 | Bardy |
| 2011/0034886 | A1 | 2/2011 | Elbe et al. |
| 2012/0283705 | A1 | 11/2012 | Lee et al. |
| 2014/0128963 | A1 | 5/2014 | Quill et al. |
| 2014/0276928 | A1 | 9/2014 | Vanderpool et al. |
| 2016/0175007 | A1 | 6/2016 | Valbuena et al. |
| 2017/0258346 | A1 | 9/2017 | Vanderpool et al. |
| 2020/0129206 | A1 | 4/2020 | Cornelius et al. |
| 2021/0153895 | A1 | 5/2021 | Vanderpool et al. |
| 2021/0267634 | A1 | 9/2021 | Vanderpool et al. |
| 2021/0267635 | A1 | 9/2021 | Vanderpool et al. |
| 2021/0267636 | A1 | 9/2021 | Vanderpool et al. |
| 2021/0275221 | A1 | 9/2021 | Vanderpool et al. |

FOREIGN PATENT DOCUMENTS

| | | |
|---|---|---|
| CN | 2702718 Y | 6/2005 |
| CN | 202342097 U | 7/2012 |
| DE | 469951 C | 1/1929 |
| DE | 4243641 A1 | 9/1994 |
| EP | 3034128 A1 | 6/2016 |
| JP | 2001502937 A | 3/2001 |
| JP | 2007516031 A | 6/2007 |
| JP | 2008528084 A | 7/2008 |
| JP | 2011092065 A | 5/2011 |
| WO | 9813091 A1 | 4/1998 |
| WO | 2005044116 A2 | 5/2005 |
| WO | 2005060306 A1 | 6/2005 |
| WO | 2008016551 A1 | 2/2008 |
| WO | 2009018008 A2 | 2/2009 |
| WO | 2012098356 A1 | 7/2012 |

OTHER PUBLICATIONS

Prosecution History from U.S. Appl. No. 17/323,298, dated Sep. 9, 2021, 14 pp.

Prosecution History from U.S. Appl. No. 17/325,873, dated Sep. 3, 2021, 14 pp.

Prosecution History from U.S. Appl. No. 17/325,904, dated Aug. 11, 2021 through Aug. 18, 2021, 25 pp.

Prosecution History from U.S. Appl. No. 17/329,986, dated Sep. 30, 2021, 17 pp.

Response to Examination Report from counterpart European Application No. 18188908.0, dated May 26, 2021, filed Sep. 30, 2021, 24 pp.

Communication pursuant to Article 94(3) EPC from counterpart European Application No. 18188908.0 dated Feb. 3, 2022, 5 pp.

Response to Examination Report dated Feb. 3, 2022, from counterpart European Application No. 18188908.0, filed May 16, 2022, 22 pp.

Notice of Allowance from U.S. Appl. No. 14/204,227 dated Nov. 3, 2021, 10 pp.

Notice of Allowance from U.S. Appl. No. 17/329,986, dated Oct. 21, 2021, 12 pp.

The Notification of Rejection, and translation thereof, from counterpart Chinese Application No. 2014-80015082.5, dated Nov. 4, 2020, 11 pp.

Final Office Action from U.S. Appl. No. 14/204,227, dated Nov. 20, 2020, 41 pp.

Examination Report from counterpart European Application No. 18188908.0, dated May 26, 2021, 7 pp.

Prosecution History from U.S. Appl. No. 14/204,227, dated Nov. 5, 2015 through May 10, 2021, 461 pp.

U.S. Appl. No. 17/323,298, filed May 18, 2021, naming inventors Vanderpool et al.

U.S. Appl. No. 17/325,873, filed May 20, 2021, naming inventors Vanderpool et al.

U.S. Appl. No. 17/325,904, filed May 20, 2021, naming inventors Vanderpool et al.

U.S. Appl. No. 17/329,986, filed May 25, 2021, naming inventors Vanderpool et al.

U.S. Patent Application No. 29/803, 137, filed Aug. 10, 2021, naming inventors Vanderpool et al.

U.S. Patent Application No. 29/803, 142, filed Aug. 10, 2021, naming inventors Vanderpool et al.

Response to Final Office Action dated Nov. 20, 2020, from U.S. Appl. No. 14/204,227, filed Jan. 8, 2021, 18 pp.

Advisory Action from U.S. Appl. No. 14/204,227, dated Jan. 28, 2021, 5 pp.

Notice of Appeal and Pre-Appeal Brief Request for Review for U.S. Appl. No. 14/204,227, filed Feb. 8, 2021, 6 pp.

U.S. Appl. No. 17/165,304, filed Feb. 2, 2021, naming inventors Vanderpool et al.

First Office Action and Search Report, and translation thereof, from counterpart Chinese Application No. 201480015082.5, dated Mar. 20, 2017, 18 pp.

(56) References Cited

OTHER PUBLICATIONS

Notice on the Second Office Action, and translation thereof, from counterpart Chinese Application No. 201480015082.5, dated Mar. 5, 2018, 9 pp.
The Decision on Rejection, and translation thereof, from counterpart Chinese Application No. 201480015082.5, dated Dec. 5, 2018, 14 pp.
Decision on Reexamination from counterpart Chinese Application No. 201480015082.5, dated Sep. 11, 2019, 11 pp.
Third Office Action, and translation thereof, from counterpart Chinese Application No. 201480015082.5, dated Apr. 7, 2020, 13 pp.
Fourth Office Action, and translation thereof, from counterpart Chinese Application No. 201480015082.5, dated Jun. 22, 2020, 13 pp.
Preliminary Amendments filed in counterpart European Patent Application No. 14717919.6, filed on Oct. 9, 2015, 9 pp.
Communication Pursuant to Rules 161(1) and 162 EPC from counterpart European Application No. 14717919.6, dated Nov. 4, 2015, 2 pp.
Response to Communication Pursuant to Rules 161(1) and 162 EPC dated Nov. 4, 2015, from counterpart European Application No. 14717919.6, filed May 13, 2016 5 pp.
Examination Report from counterpart European Application No. 14717919.6, dated Jul. 28, 2017, 5 pp.
Response to Examination Report dated Jul. 28, 2017, from counterpart European Application No. 14717919.6, filed Dec. 6, 2017, 13 pp.
Intent to Grant from counterpart European Application No. 14717919.6, dated Apr. 16, 2018, 30 pp.
Decision to Grant from counterpart European Application No. 14717919.6, dated Jun. 9, 2018, 1 pp.
Extended European Search Report from counterpart European Patent Application No. 18188908.0, dated Oct. 19, 2018, 7 pp.
Response to Communication Pursuant to Rule 69 EPC dated Jan. 7, 2019 and the Extended European Search Report dated Oct. 19, 2018, from counterpart European Application No. 18188908.0, filed Apr. 15, 2019, 13 pp.
Office Action, and translation thereof, from counterpart Japanese Patent Application No. 2016-501382, dated Oct. 29, 2017, 7 pp.
Decision to Grant, and translation thereof, from counterpart Japanese Application No. 2016-501382, dated Jun. 26, 2018, 5 pp.
Notice of Reasons for Refusal, and translation thereof, from counterpart Japanese Application No. 2018-137778, dated Jun. 25, 2019, 15 pp.
Notice of Reasons for Refusal, and translation thereof, from counterpart Japanese Application No. 2018-137778, dated Jun. 28, 2019, 12 pp.
Office Action, and translation thereof, from counterpart Japanese Application No. 2018137778, dated Feb. 6, 2020, 3 pp.
International Search Report and the Written Opinion from International Application No. PCT/US2014/023912, dated Jun. 20, 2014, 9 pp.
International Preliminary Report on Patentability from International Application No. PCT/US2014/023912, dated Sep. 15, 2015, 5 pp.
Prosecution History from U.S. Appl. No. 14/204,227, dated Nov. 5, 2015 through Aug. 3, 2020, 332 pp.
Prosecution History from U.S. Appl. No. 15/610,076, dated Aug. 7, 2017 through Aug. 3, 2020, 227 pp.
U.S. Appl. No. 29/748,593, filed Aug. 31, 2020, naming inventors Vanderpool et al.
U.S. Appl. No. 29/748,588, filed Aug. 31, 2020, naming inventors Vanderpool et al.
Office Action from U.S. Appl. No. 17/165,304 dated Feb. 2, 2023, 15 pp.
Notice of Allowance from U.S. Appl. No. 17/165,304 dated Jun. 1, 2023, 10 pp.
Notice of Intent to Grant and Text Intended to Grant from counterpart European Application No. 18188908.0 dated Mar. 15, 2023, 36 pp.
Response to Office Action dated Feb. 2, 2023 from U.S. Appl. No. 17/165,304, filed May 2, 2023, 11 pp.

* cited by examiner

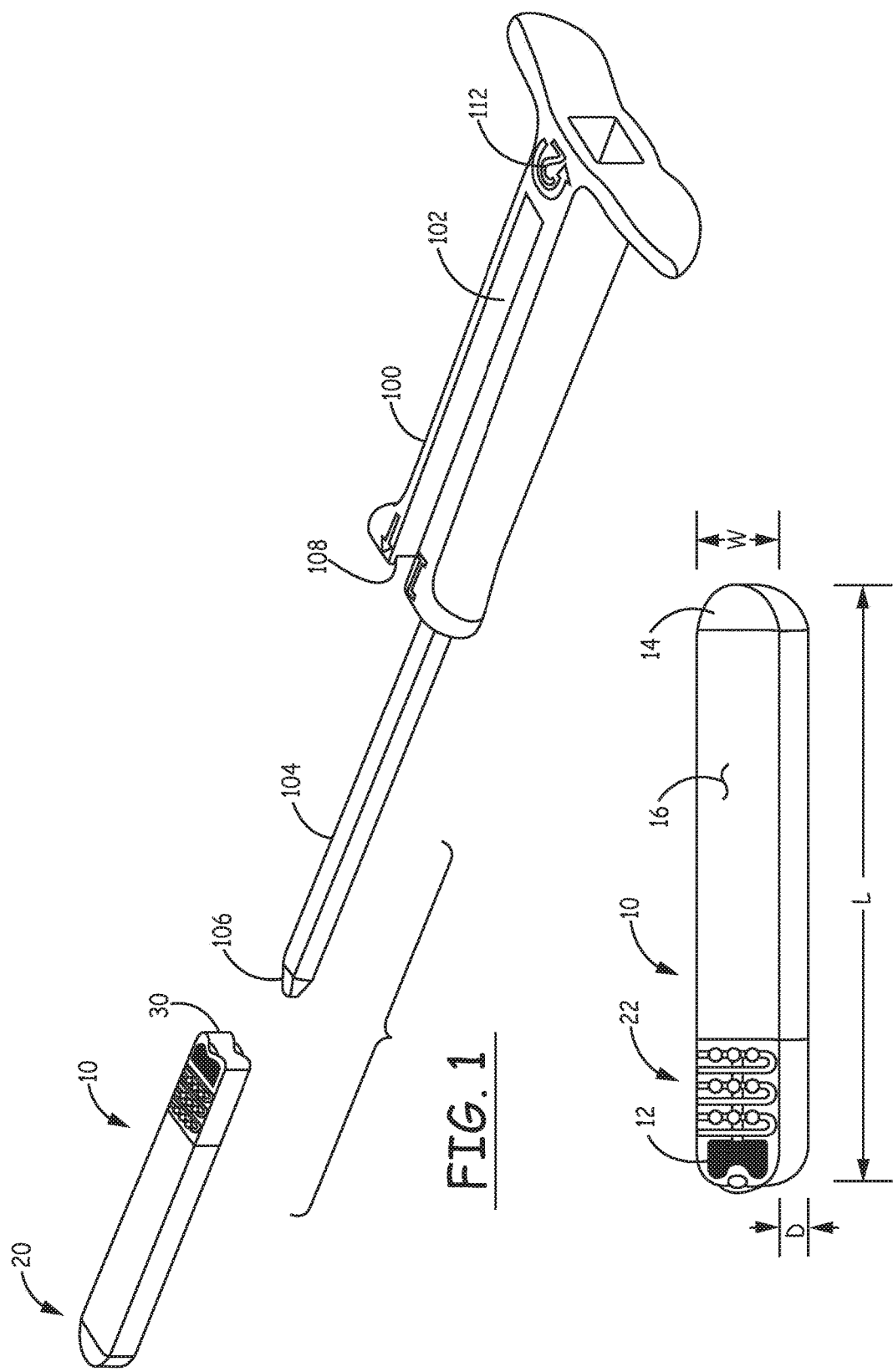

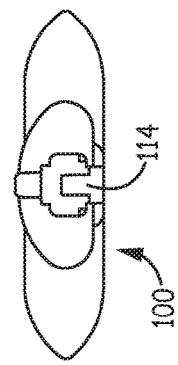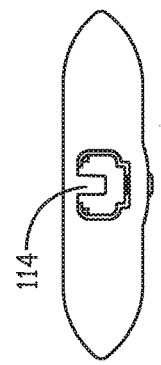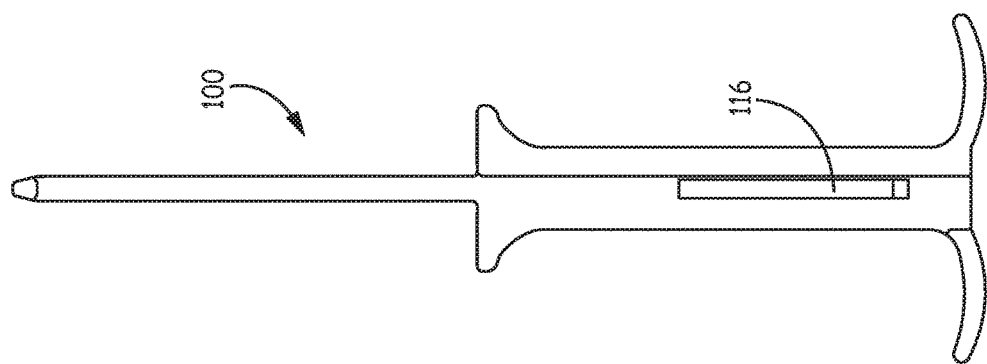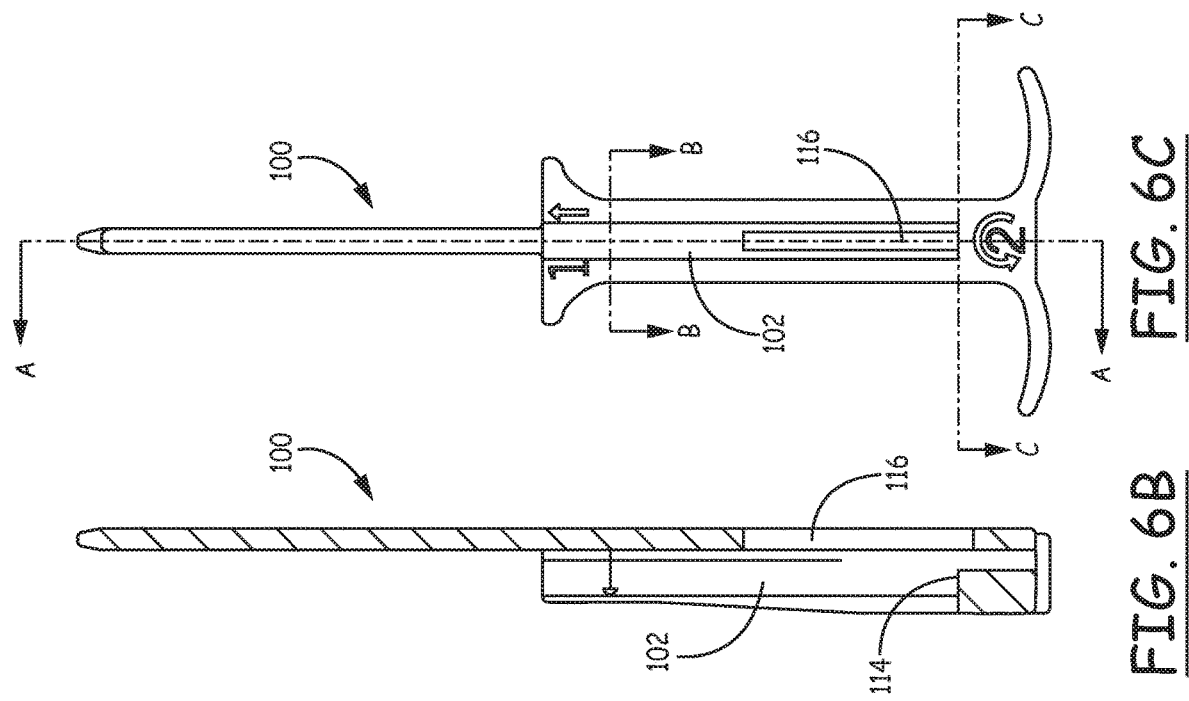

SUBCUTANEOUS DELIVERY TOOL

This application is a continuation of U.S. patent application Ser. No. 15/610,076, filed May 31, 2017, which is a continuation of U.S. patent application Ser. No. 14/204,227, filed Mar. 11, 2014, which claims the benefit of U.S. Provisional Application No. 61/788,940, filed Mar. 15, 2013. The entire content of each of these applications is incorporated herein by reference.

BACKGROUND

The use of monitoring equipment to measure various physical parameters of a patient is well known. There is a growing demand for using subcutaneous monitoring devices, which allow doctors to obtain information without a patient being connected to an external machine and/or which may otherwise not be reproducible in office settings. The term subcutaneous generally implies locations within the body of a patient under the skin and exterior to the musculature beneath the skin. For example, an implantable device that includes the ability to monitor a patient's heart beat in order to detect transient symptoms suggesting cardiac arrhythmia allows doctors to review data over a longer period of time than using external monitoring equipment in a simulated testing situation. However, to successfully implant implantable subcutaneous devices an implantation tool should, for example, ensure that the device is not implanted in muscle, reduce contact between the surgeon and the wound, be used in an office setting to minimize patient discomfort and the need for invasive surgery and have the ability to repeatedly recreate the same size incision site in the patient.

Exemplary prior art insertion tools include those illustrated in US Patent Application Publication No. 2010/0094252 by Wengreen, et al., incorporated herein by reference in its entirety.

SUMMARY

Further areas of applicability will become apparent from the description provided herein. It should be understood that the description and specific examples are intended for purposes of illustration only and are not intended to limit the scope of the present disclosure.

Exemplary embodiments provide subcutaneous implantation tools and methods of implanting a subcutaneous micro-device using the same. The invention provides a syringe-like tool, comprising a tool body, hereafter "handle", having a hollow, distally longitudinally extending recess such as a bore or channel and having a distal opening through which the device may be delivered. The device preferably also includes a movable plunger located within the bore or channel. An incision tool is provided to make an incision through which the subcutaneous device is implanted.

The device may, for example, be implanted in the region of the thorax. A specific recommended location will typically be provided within an associated product manual. In one embodiment, two electrodes on the body of the device monitor the patient's subcutaneous ECG. The device may ECG recordings in response to patient activation or in response to automatically detected arrhythmias. Exemplary devices are disclosed in US Patent Application Publication No. 2009/0036917 by Anderson, US Patent Application Publication No. 2010/0094252 by Wengreen, et al., US Patent Application Publication No. 2012/0283705 by Hoeppner, et al., U.S. Pat. No. 5,987,352, issued to Klein, et al., U.S. Pat. Nos. 6,412,490 and 7,035,684 issued to Lee, et al. and U.S. Pat. No. 6,230,059, issued to Duffin, et al., all incorporated herein by reference in their entireties.

The incision tool is designed to create an incision of repeatable width and depth with a single motion. It is composed of a blade, designed to make a repeatable incision, and handle, designed to ergonomically fit the hand. The incision tool is intended to make the incision simple and repeatable. Other mechanisms for making openings in the patient's skin such as trocars, spreaders, scalpels and the like may be substituted in some alternative embodiments. The insertion tool delivers the device through the incision and into the subcutaneous tissue. The tool is designed to ensure the device is delivered into a tight pocket to maximize electrode contact with the surrounding tissue in a highly repeatable manner, and is composed of two parts: a handle and a plunger. The handle is composed of a bore or channel section, used to hold the device and guide it during implant, and a protrusion extending distally of the channel, used to bluntly dissect an implant path for the device to travel down while being implanted. The tunneler extends distally from the channel a position laterally displaced from the device when the device is located in the channel. The plunger is used to push the device distally out of the handle, through the incision, alongside and exterior to the tunneler and along the implant path created by the tunneler to the final implant location.

The device is typically loaded into the channel section of the insertion tool handle and sterile packaged along with both the insertion tool plunger and the incision tool.

The device is locatable within the channel distal to the plunger, so that when the plunger is moved distally, the device advances distally out of the tool body and into the tissue. Typically, the device will take the form of an elongated body, having a length greater than its thickness and width, as illustrated in the published Application No. 2010/0094252, cited above. The device may extend along its longitudinal axis between proximal and distal ends. The longitudinal channel or bore of the tool body may conform at least in part to the outer configuration of the device and more typically to a cross section of the device taken along its longitudinal axis. If the device, like the above discussed device, has a width greater than its depth and/or is otherwise radially asymmetric around its longitudinal axis, this feature allows the device to be advanced into the tissue while maintaining a desired orientation, as discussed in more detail below.

Optimally, the final insertion site of the device is located a short distance from the incision site. As noted above, the handle is preferably provided with an elongated protrusion or tunneler extending distally from the distal opening of the bore, which is insertable into the tissue through the incision to create a path in the tissue, along which the device may be advanced when pushed by the plunger. The distal end of the tunneler when so inserted is preferably located at the desired location of the distal end of the device. The length of the tunneler is thus preferably at least equal to and preferably somewhat greater than the length of the subcutaneous device.

Additional embodiments provide methods of implanting a subcutaneous micro-device, including inserting the dissection body of the tool described by the embodiments of the tool into an implantation site, where the dissection body includes a micro-device, and delivering the micro-device.

BRIEF DESCRIPTION OF DRAWINGS

Exemplary embodiments will be more clearly understood from the following detailed description taken in conjunction with the accompanying drawings. FIGS. 1-10 represent non-limiting, example embodiments as described herein.

FIG. 1 is a perspective view of an exemplary implantable device and the associated tool handle.

FIG. 2 is a perspective view of the exemplary implantable device.

FIG. 3 is a perspective view of the incision tool according to exemplary embodiments.

FIGS. 6A, 6B, 6C, 6D and 6E are distal end, cut-away, top, bottom and proximal end views, respectively, of the tool handle.

FIG. 10 is a flow chart illustrating a method of delivering a device to a subcutaneous site according to exemplary embodiments.

DETAILED DESCRIPTION

Figure 3:
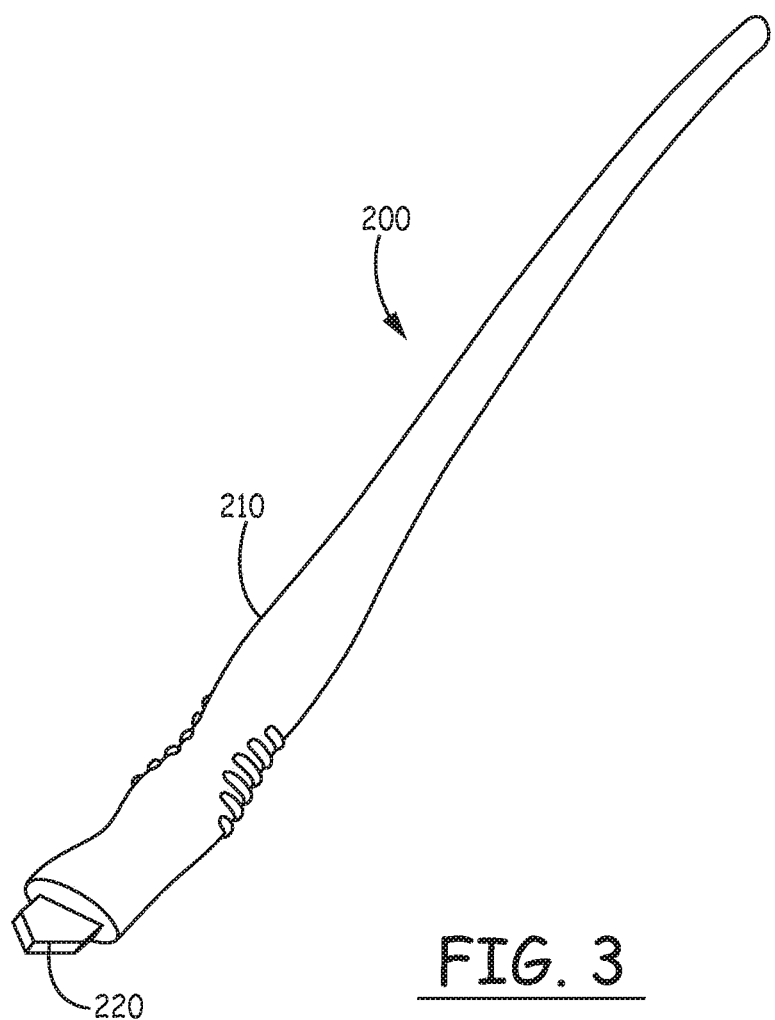

Various exemplary embodiments will now be described more fully with reference to the accompanying drawings in which some exemplary embodiments are illustrated. In the drawings, the thicknesses of layers and regions may be exaggerated for clarity.

Accordingly, while exemplary embodiments are capable of various modifications and alternative forms, embodiments thereof are shown by way of example in the drawings and will herein be described in detail. It should be understood, however, that there is no intent to limit exemplary embodiments to the particular forms disclosed, but on the contrary, exemplary embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of exemplary embodiments. As used herein, the term "and/or" includes any and all combinations of one or more of the associated listed items.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Other words used to describe the relationship between elements should be interpreted in a like fashion (e.g., "between" versus "directly between," "adjacent" versus "directly adjacent," etc.).

The terminology used herein is for the purpose of describing only particular embodiments and is not intended to be limiting of exemplary embodiments. As used herein, the singular forms "a," "an" and "the" are intended to include the plural forms as well, unless the context clearly indicates otherwise. It will be further understood that the terms "comprises," "comprising," "includes" and/or "including," when used herein, specify the presence of stated features, integers, steps, operations, elements and/or components, but do not preclude the presence or addition of one or more other features, integers, steps, operations, elements, components and/or groups thereof.

Spatially relative terms, e.g., "beneath," "below," "lower," "above," "upper" and the like, may be used herein for ease of description to describe one element or a relationship between a feature and another element or feature as illustrated in the figures. It will be understood that the spatially relative terms are intended to encompass different orientations of the device in use or operation in addition to the orientation depicted in the Figures. For example, if the device in the figures is turned over, elements described as "below" or "beneath" other elements or features would then be oriented "above" the other elements or features. Thus, for example, the term "below" can encompass both an orientation which is above as well as below. The device may be otherwise oriented (rotated 90 degrees or viewed or referenced at other orientations) and the spatially relative descriptors used herein should be interpreted accordingly.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which exemplary embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Exemplary embodiments are directed to subcutaneous implantation tools and methods of implanting subcutaneous micro-devices. FIGS. 1A to 10 illustrate various exemplary embodiments of such subcutaneous implantation tools.

FIG. 1 shows the implantable device 10, aligned longitudinally with the handle 100, arranged for the insertion of device 10 into the channel 102 of the handle 100. The proximal end 20 of the device is inserted into the distal end 108 of the channel 102 of the handle and is advanced proximal until the proximal end 30 of the device is located adjacent an internal stop surface (not illustrated) within the handle 100. At this point, the distal end 20 of the device will be adjacent the distal end 108 of the handle 100. The open upper portion of the channel 102 allows visual verification that the device 10 is properly inserted into the channel. The tunneler 104 extends distally of the distal end 108 of channel 102. The distal end 106 of the tunneler is placed into the incision made by the incision tool with its upper surface facing outward of the patient's body and advanced to provide blunt dissection of the subcutaneous tissue to a point where the distal end 20 of the device is adjacent the opening of the incision. The handle 100 is then rotated 180 degrees so that the tunneler 104 is then above the device (outward relative to the patient's skin). This allows upward pressure on the handle to assist in temporarily enlarging the incision and assures that the device will not escape as advanced distally into the tissue. The device 10 is then advanced by distal movement of the plunger illustrated in FIG. 5B within the channel 102 and along the tunneler 104 until it is properly located within the tissue, displaced distally a short distance from the opening of the incision. The logo 112 assists in reminding the physician to rotate the handle prior to insertion of the plunger and advancement of the device.

FIG. 2 shows the device 10 in more detail. In this view it can be seen that the device comprises two electrodes 12 and 14, located adjacent the proximal and distal ends, respectively, of the device. When implanted, electrode 12, located on the upper surface 16 of the device preferably faces outward toward the skin. As such, when the device is placed into the handle as discussed above, the electrode 12 faces downward and is not visible through the open upper portion of the channel, allowing verification of proper insertion into the handle.

The exemplary device 10 as illustrated generally takes the form of an elongated rectangular prism having rounded corners and a rounded distal end portion. The rounded distal end of the device assists in allowing it to advance into body tissue, providing blunt dissection of the tissue as it advances. Because the cross section of the device is substantially greater than the cross section of the tunneler, the device will be located snugly within the tissue, reducing the chances for the formation of air bubbles adjacent the electrodes and also assisting in maintaining the device in its desired position. The device has length (L), width (W) and depth (D) as illustrated. In this particular embodiment, the with is greater than the depth, providing radial asymmetry along the longitudinal axis of the device and assisting in maintaining the device in its proper orientation with upper surface 16 facing outward after implant. A suture hole 18 may optionally be provided at the proximal end of the device to allow the physician to suture it to underlying tissue if desired. Projections 22 may optionally be provided to prevent longitudinal movement of the device after implant.

As discussed above, the inner surface of the channel of the handle is preferably configured to correspond to the outer configuration of the device. As discussed below in more detail, the configuration of the channel of the handle is configured to engage the rounded corners of the device, preventing rotation of the device within the handle.

FIG. 3 illustrates the incision tool 200, which is provided with a curved plastic handle 210 fitted with a flat, pointed blade 220 having a width equal to the desired width of the incision. The handle is designed to be comfortably held in a position allowing the blade to be advanced through the skin at a shallow angle, avoiding damage to underlying muscle tissue.

Figure 4A:
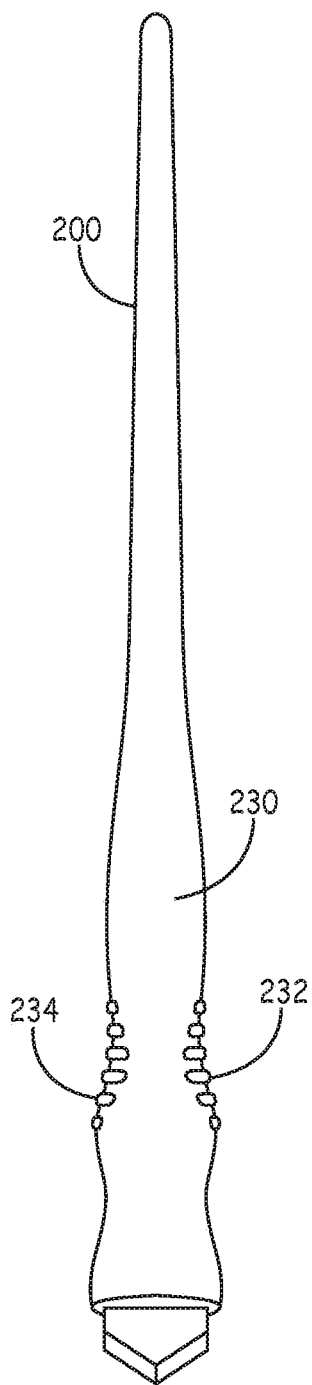
FIGS. 4A, 4B and 4C are top, side and bottom views, respectively, of the incision tool of FIG. 3.
Figure 4B:
Figure 4C:
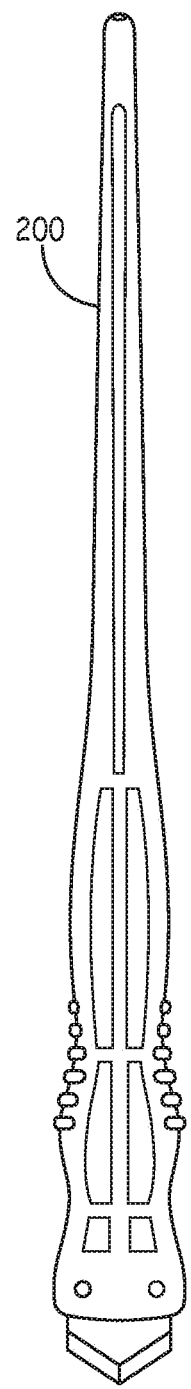

FIGS. 4A, 4B and 4C show top, side and bottom views of the incision device 200. As illustrated in 4A, both the differing coloration of the finger grips 234 and 232 and the placement of the logo 236 on the upper surface assist the physician in assuring that the orientation of the blade is correct to provide the desired shallow penetration angle.

Figure 5A:
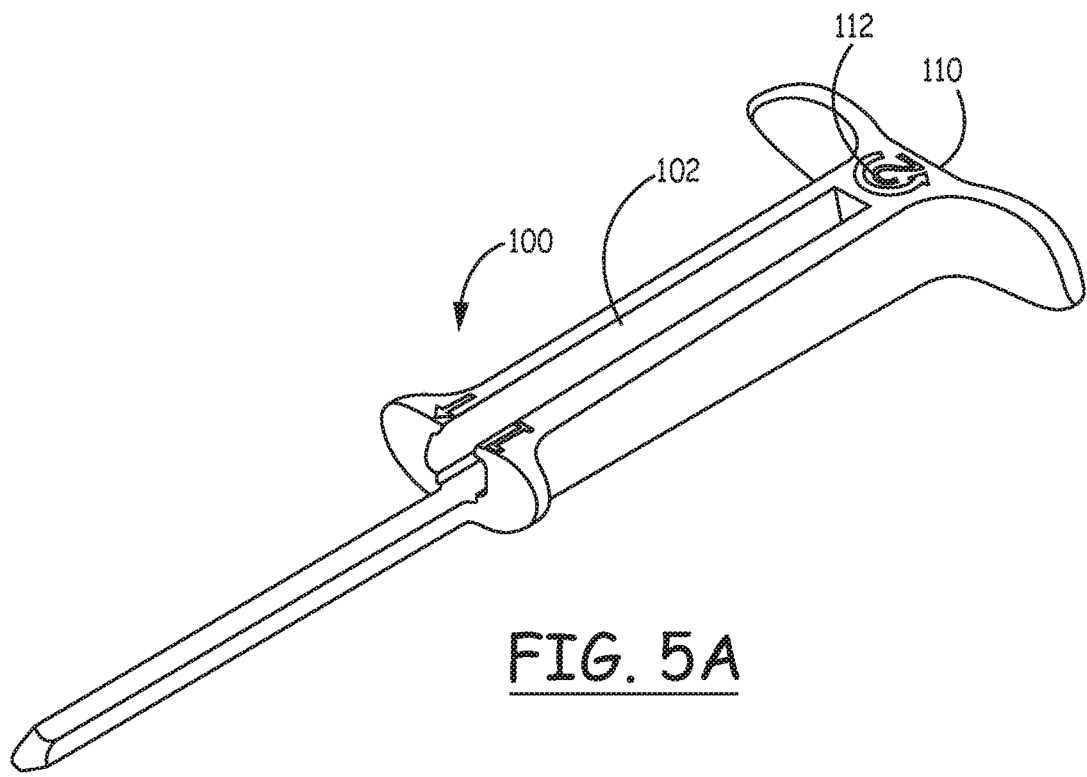
FIGS. 5A and 5B are perspective views of the tool handle and plunger, respectively, according to exemplary embodiments of the invention.
Figure 5B:
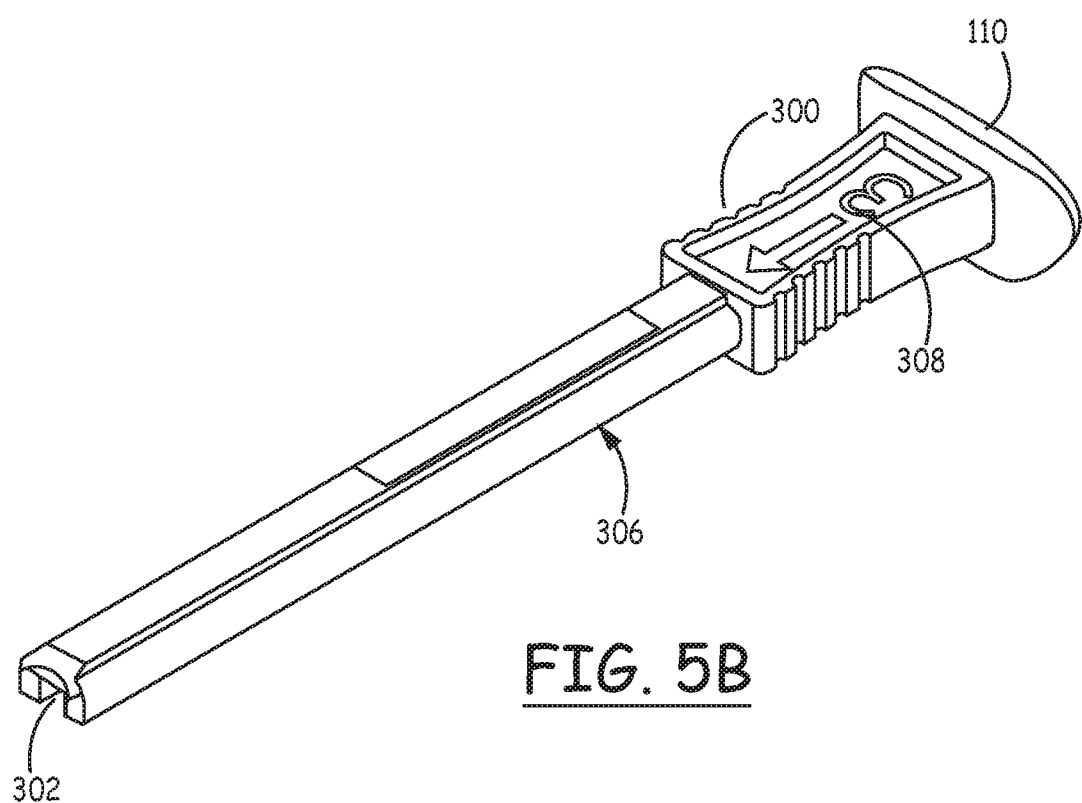

FIGS. 5A and 5B show the handle 100 and the plunger 300 prior to insertion of the plunger into the handle. After rotation of the handle so that its upper surface bearing marking 112 now faces inward toward the patient's skin, the distal end 302 of plunger 300 is then inserted into an opening in the proximal end 110 of the handle and into the channel 102 of the handle.

The plunger is provided with a groove 306 running the length of the lower surface of the plunger up to a distal stop surface discussed below. The opening in the proximal end of the handle includes a protrusion corresponding to the groove in the lower surface of the plunger, assuring its proper orientation within the handle. A marking 308 adjacent the proximal end of the plunger assists the physician in determining that the plunger is in the proper orientation for insertion into the handle.

The plunger is advanced distally, pushing the device into the incision along the then inward facing surface of the tunneler. The device thus follows the path defined by the tunneler to assure proper placement within the tissue. After insertion of the device, the handle and plunger are removed.

Various medical grade materials may be used to form the various parts of the subcutaneous implantation tool, for example, plastics, metals, rubber, sanitizable materials, etc. Exemplary embodiments of the subcutaneous implantation tool may be inexpensive, disposable, etc. The subcutaneous implantation tool may also be configured to be used with known automated injection systems, which use, e.g., compressed air or other inert gases in place of a manual plunger.

FIGS. 6A, 6B, 6C, 6D and 6E are distal end, cut-away, top, bottom and proximal end views, respectively, of the tool handle 100. In these views the projection 114 is visible. Projection 114 provides a distal facing stop surface limiting the insertion of the device 10 into the channel 102. It further engages the slot in the lower surface of the plunger 300, assuring proper orientation of the plunger within the handle. It also provides a proximal facing stop surface limiting distal movement of the plunger. The handle is also show as optionally provided with a slot 116 in its lower surface, through which advancement of the plunger and device can be observed.

Figure 7A:
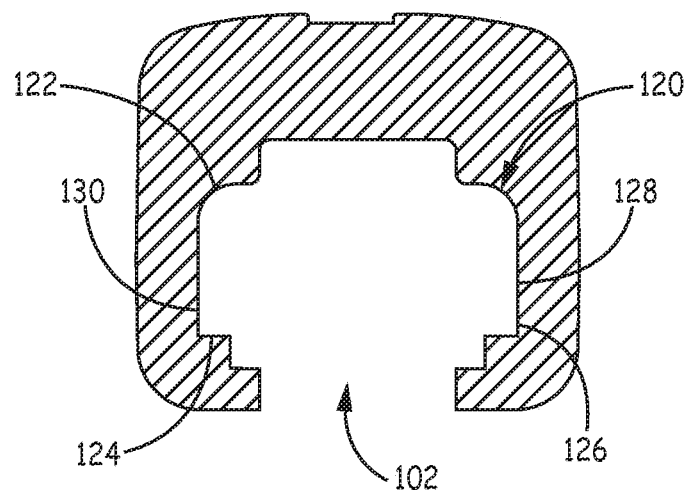
FIGS. 7A and 7B are cross sectional views through the tool handle as illustrated in FIG. 6C.
Figure 7B:
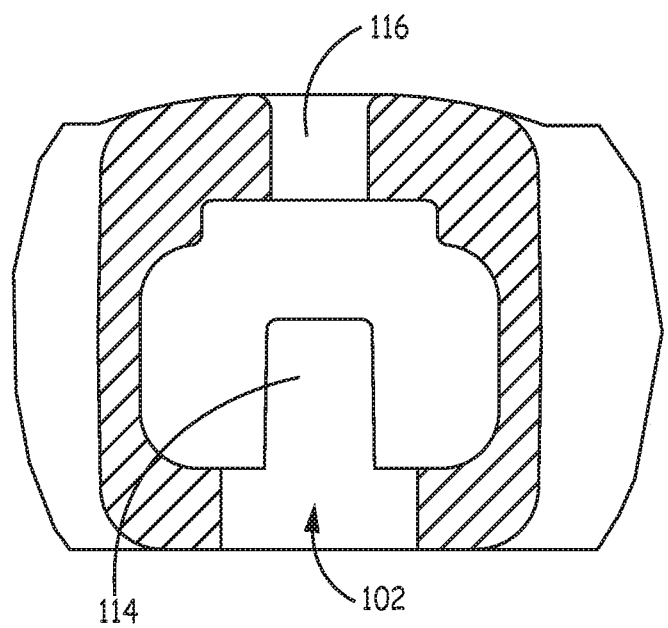

FIGS. 7A and 7B are cross sectional views through the tool handle as illustrated in FIG. 6C. In these views, the arrangement of the inner corner surfaces 12, 122, 124 and 126 can be seen. These surfaces, along with side surfaces 128 and 130, are arranged to generally correspond to the corners and the side surfaces of the device, preventing rotation of the device within the handle. The distal facing surface of projection 114 is also visible in this view.

FIGS. 8A, 8B, 8C and 8D are distal end, cut-away, top and proximal end views, respectively, of the plunger of 5B. In these figures, the configuration of the groove 306 can be seen, along with distally facing stop surface 310, which engages with the proximal facing surface of protrusion 114 of the handle, to limit distal movement of the plunger.

Figure 8B:
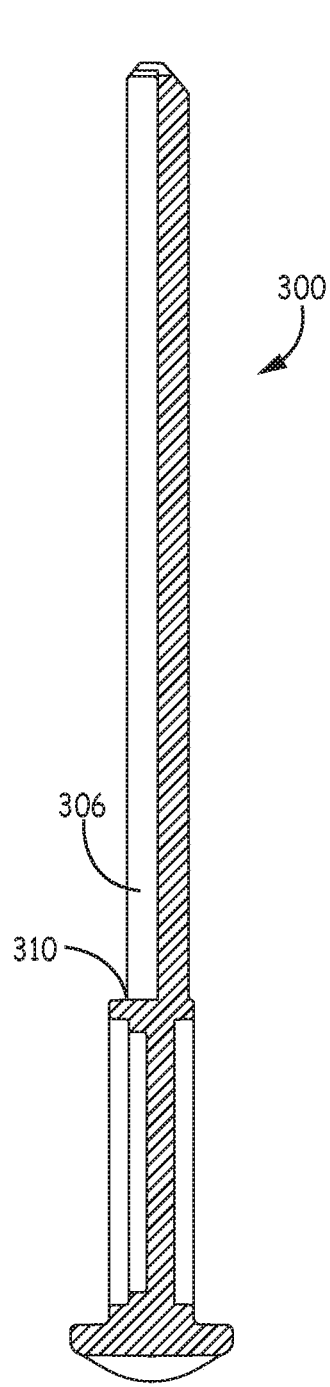
FIGS. 8A, 8B, 8C and 8D are distal end, cut-away, top and proximal end views, respectively, of the plunger of 5B.
Figure 8C:
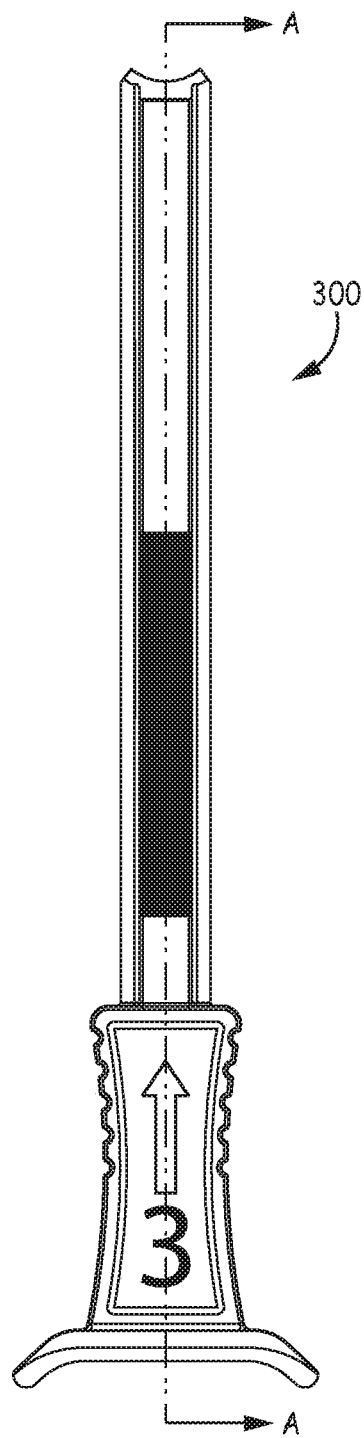
Figure 8A:
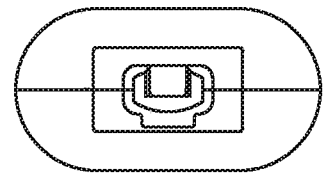
Figure 8D:
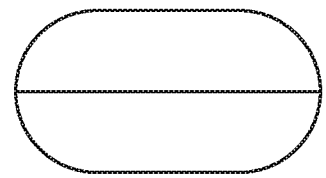
Figure 9A:
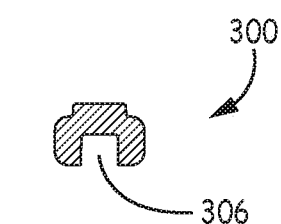
FIGS. 9A, 9B, and 9C are cross sectional, side and bottom views, respectively, of the plunger as illustrated in FIG. 8D.
Figure 9B:
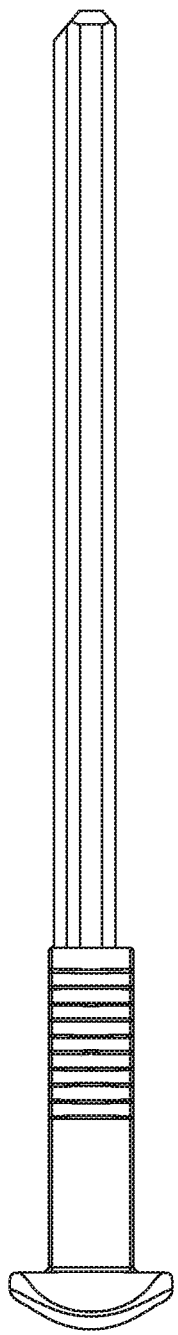
Figure 9C:
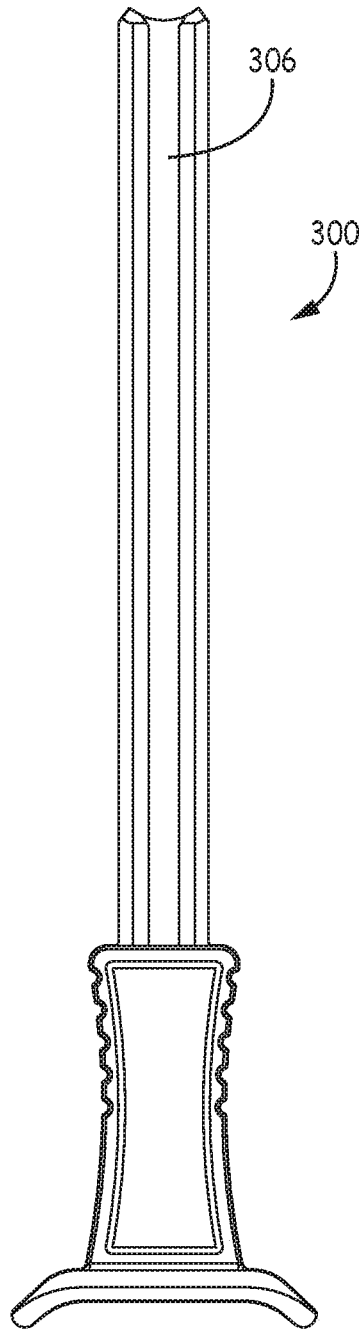

FIGS. 9A, 9B, and 9C are cross sectional, side and bottom views. Respectively, of the plunger as illustrated in FIG. 8D. In these views, the configuration of the groove 306 is visible in more detail.

Figure 10:
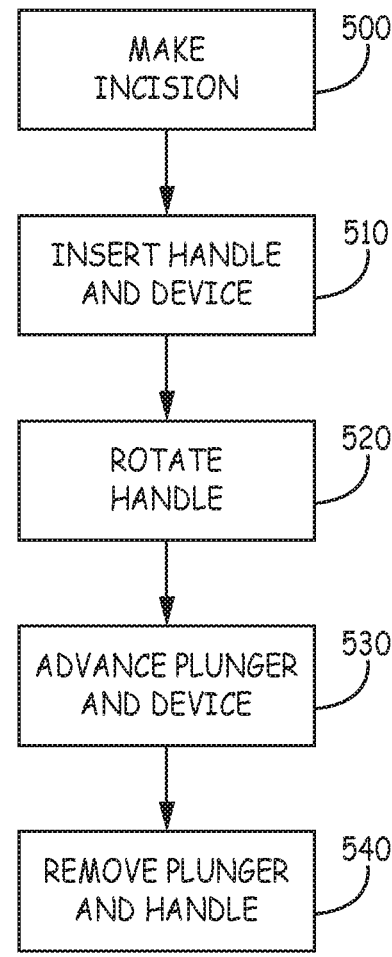

FIG. 10 is a flow chart illustrating a preferred embodiment of an insertion process according to the present invention. At 500, the incision is made using the incision tool. At 510, the handle carrying the device is inserted into the tissue such that the tunneler produces an elongated blunt incision along which the device may be advanced. In this step, the device is located outward of the tunneler relative to the patient's body. At 520 the handle, carrying the device is rotated so that the device is now inward of the tunneler relative to the patient's body. At 530, the device is advanced by the plunger along the handle and along the then inward facing surface of the tunneler subcutaneously into the patient's body. Finally, at 540, the handle and tunneler are removed.

Exemplary embodiments thus described allow for subcutaneous implantation of devices that are minimally invasive. Note that exemplary embodiments may be used in both human and animal patients.

Exemplary embodiments of the present invention being thus described, it will be obvious that the same may be varied in many ways. Such variations are not to be regarded as a departure from the spirit and scope of the exemplary embodiments of the invention, and all such modifications as would be obvious to one skilled in the art are intended to be included within the scope of the invention.

What is claimed is:

1. An implantation device for implanting a medical device in subcutaneous tissue, wherein the implantation device comprises:
   a tool body, wherein the tool body comprises:
      a first tool body portion including a first proximal end and a first distal end; and
      a second tool body portion defining a channel, the second tool body portion including a second proximal end and a second distal end,
      wherein the first proximal end of the first tool body portion adjoins the second distal end of the second tool body portion,
      wherein a longest dimension of a cross section of the first tool body portion is less than a longest dimension of a cross section of the second tool body portion,
      wherein the cross section of the first tool body portion and the cross section of the second tool body portion correspond to a location in which the first proximal end of the first tool body portion adjoins the second distal end of the second tool body portion, and
      wherein a first surface of the second tool body portion defines a distal opening of the channel at the second distal end of the second tool body portion, and wherein an area of a second surface of the second tool body portion defines a lateral opening separate from the distal opening, wherein the first surface that defines the distal opening includes an outer surface of the second tool body portion at the second distal end of the second tool body portion; and
   a plunger, wherein a distal end of the plunger is configured to push a proximal end of the medical device out of the channel through the distal opening.

2. The implantation device of claim 1, wherein the first tool body portion extends distally from the second distal end of the second tool body portion.

3. The implantation device of claim 1, wherein the lateral opening allows visualization of an entire length of the medical device within the channel from a position lateral to the tool body, and wherein the entire length of the medical device extends from a proximal end of the medical device to a distal end of the medical device.

4. The implantation device of claim 3, wherein the channel is configured to receive the entire length of the medical device from the proximal end of the medical device to the distal end of the medical device.

5. The implantation device of claim 1, wherein the first surface of the second tool body portion is normal to the second surface of the second tool body portion.

6. The implantation device of claim 1, wherein the area of the second surface of the second tool body portion which defines the lateral opening represents a first area of the second surface, wherein the second surface further includes a second area which represents a lateral surface, and wherein the second area is proximal to the first area on the second tool body portion.

7. The implantation device of claim 1,
   wherein the second tool body portion defines a projection into the channel, and
   wherein the plunger defines a groove that corresponds to and engages with the projection into the channel.

8. The implantation device of claim 7, wherein the projection and the groove are configured to limit longitudinal movement of the plunger within the channel.

9. The implantation device of claim 7, wherein the projection is located within the channel proximal to the distal opening of the channel.

10. The implantation device of claim 1, wherein the first distal end of the first tool body portion is configured for blunt dissection of the subcutaneous tissue.

11. The implantation device of claim 1, wherein the distal end of the plunger is movable distally beyond the distal opening of the channel to displace the medical device beyond the distal opening of the channel.

12. A system for implanting a medical device in subcutaneous tissue, wherein the system comprises:
   the medical device; and
   an implantation device comprising:
      a tool body, wherein the tool body comprises:
         a first tool body portion including a first proximal end and a first distal end; and
         a second tool body portion defining a channel, the second tool body portion including a second proximal end and a second distal end,
         wherein the first proximal end of the first tool body portion adjoins the second distal end of the second tool body portion,
         wherein a longest dimension of a cross section of the first tool body portion is less than a longest dimension of a cross section of the second tool body portion,
         wherein the cross section of the first tool body portion and the cross section of the second tool body portion correspond to a location in which the first proximal end of the first tool body portion adjoins the second distal end of the second tool body portion, and
         wherein a first surface of the second tool body portion defines a distal opening of the channel at the second distal end of the second tool body portion, and wherein an area of a second surface of the second tool body portion defines a lateral opening separate from the distal opening, wherein the first surface that defines the distal opening includes an outer surface of the second tool body portion at the second distal end of the second tool body portion; and
      a plunger, wherein a distal end of the plunger is configured to push a proximal end of the medical device out of the channel through the distal opening.

13. The system of claim 12, wherein the first tool body portion extends distally from the second distal end of the second tool body portion.

14. The system of claim 12, wherein the lateral opening allows visualization of an entire length of the medical device within the channel from a position lateral to the tool body, and wherein the entire length of the medical device extends from a proximal end of the medical device to a distal end of the medical device.

15. The system of claim 14, wherein the channel is configured to receive the entire length of the medical device from the proximal end of the medical device to the distal end of the medical device.

16. The system of claim 12, wherein the first surface of the second tool body portion is normal to the second surface of the second tool body portion.

17. The system of claim 12, wherein the area of the second surface of the second tool body portion which defines the lateral opening represents a first area of the second surface, wherein the second surface further includes a second area which represents a lateral surface, and wherein the second area is proximal to the first area on the second tool body portion.

18. The system of claim 12,
wherein the second tool body portion defines a projection into the channel, and
wherein the plunger defines a groove that corresponds to and engages with the projection into the channel.

19. The system of claim 12, the first distal end of the first tool body portion is configured for blunt dissection of the subcutaneous tissue.

20. The system of claim 12, wherein the distal end of the plunger is movable distally beyond the distal opening of the channel to displace the medical device beyond the distal opening of the channel.

* * * * *